(12) United States Patent
Lim et al.

(10) Patent No.: US 7,880,024 B2
(45) Date of Patent: Feb. 1, 2011

(54) IONIC LIQUIDS MISCIBLE WITH VARIOUS POLAR/NON-POLAR SOLVENTS AND METHOD OF PREPARING THE SAME

(75) Inventors: Myong Hoon Lim, Yongin (KR); Young Mi Kim, Yongin (KR); Jae Eun Rho, Yongin (KR); Jae Hoi Gu, Seongnam (KR); Yong Ho Yu, Seongnam (KR)

(73) Assignee: Samsung Engineering Co., Ltd., Gangnam-Gu, Seoul (KR)

( * ) Notice: Subject to any disclaimer, the term of this patent is extended or adjusted under 35 U.S.C. 154(b) by 329 days.

(21) Appl. No.: 12/149,034

(22) Filed: Apr. 25, 2008

(65) Prior Publication Data
US 2009/0253924 A1    Oct. 8, 2009

(30) Foreign Application Priority Data
Apr. 2, 2008    (KR) .................. 10-2008-0030801

(51) Int. Cl.
*C07F 9/02*    (2006.01)
(52) U.S. Cl. ..................... 554/78; 554/85; 554/103
(58) Field of Classification Search ............. 554/78, 554/85, 103
See application file for complete search history.

(56) References Cited

U.S. PATENT DOCUMENTS

| 5,700,841 | A | * | 12/1997 | Walker ................ 514/642 |
| 5,731,101 | A |   | 3/1998  | Sherif et al. |
| 5,827,602 | A |   | 10/1998 | Koch et al. |
| 7,208,605 | B2 |  | 4/2007  | Davis, Jr. |
| 7,252,791 | B2 |  | 8/2007  | Wasserscheid et al. |

FOREIGN PATENT DOCUMENTS

| EP | 2 003 157 | | 12/2008 |
| GB | 2 412 912 | | 10/2005 |
| JP | 1020070022772 A | | 2/2007 |
| WO | WO 02/26701 | | 4/2002 |
| WO | WO 0226701 A2 | * | 4/2002 |
| WO | WO 03/051894 | | 6/2003 |
| WO | WO 03051894 A1 | * | 6/2003 |
| WO | WO 2005/097729 | | 10/2005 |
| WO | WO 2005097729 A2 | * | 10/2005 |

OTHER PUBLICATIONS

Office Action in GB 0905007.1 dated Jul. 3, 2009.
Korean Office Actin dated Jan. 29, 2010, issued in corresponding Korean application.
A.P. Abbott, J.C. Barron, K.S. Ryder, D. Wilson, Chem.-Eur. J. 13, 2007, 6495-6501.

* cited by examiner

*Primary Examiner*—Deborah D Carr
(74) *Attorney, Agent, or Firm*—Buchanan Ingersoll & Rooney PC

(57) ABSTRACT

Provided are an ionic liquid and a method of preparing the same. The ionic liquid includes at least one type of compound represented by $(Cat^+)(R'COO^-)$. Here, the $Cat^+$ is a cation selected from the group consisting of quaternary ammonium, quaternary phosphonium, sulfonium, imidazolium, pyridinium, pyrazolium, piperidinium, pyrrolium, pyrrolidinium, triazolium, and a mixture of two or more thereof, and R' is a hydrocarbon comprising at least one unsaturated bond, and having 4 to 30 carbon atoms. The ionic liquid is partially or completely miscible with various polar and/or non-polar solvents, and may be used as a solvent, a solvent additive, an electrolyte, a heat carrier, a charge carrier, a heat carrier additive, a charge career additive, or a phase transfer catalyst, at room temperatures and below. Furthermore, the cost of manufacturing the ionic liquid can be reduced.

7 Claims, No Drawings

IONIC LIQUIDS MISCIBLE WITH VARIOUS POLAR/NON-POLAR SOLVENTS AND METHOD OF PREPARING THE SAME

CROSS-REFERENCE TO RELATED PATENT APPLICATION

This application claims the benefit of Korean Patent Application No. 10-2008-0030801, filed on Apr. 2, 2008, in the Korean Intellectual Property Office, the disclosure of which is incorporated herein in its entirety by reference.

BACKGROUND OF THE INVENTION

1. Field of the Invention

The present invention relates to ionic liquids and a method of preparing the same, and more particularly, to ionic liquids and a method of preparing the same, whereby the ionic liquids are partially or completely miscible with various polar and/or non-polar solvents, and can be used as a phase transfer catalyst at room temperature, thereby reducing manufacturing costs. Examples of the polar or non-polar solvent may include water, or various organic solvents such as alcohols, acids, olefins, paraffins, aromatics, aliphatics, amines, ethers, esters, ketones, aldehydes, amides, nitriles, and nitroalkanes.

2. Description of the Related Art

In general, ionic liquids are defined as molten salts with melting point below 100° C. Due to their relatively low melting point, ionic liquids can be used as solvent or co-solvent where chemical reaction may be carried out. The applications of ionic liquids are rapidly growing in various technical fields because their chemical and physical characteristics can be readily modulated by tailoring the natures of cation and anion.

According to U.S. Pat. Nos. 5,827,602, 5,731,101, and 7,208,605, certain types of ionic liquids can be used in the applications of non-aqueous batteries, electrochemical capacitors, electroplating, catalysis and chemical separations. Since ionic liquids solely consist of a pair of ions (cation and anion) rather than molecules, it has shown very special distinctiveness, such as high reactivity and specific selectivity, in comparison with ordinary organic solvent.

Solvent properties, such as melting/boiling points, viscosity, solubility, or polarity, always influence the overall performance of chemical reactions as well as other applications. In this aspect, a great number of efforts have been made to tailor those properties of ionic liquids for desirable properties. U.S. Pat. No. 5,731,101 discloses low temperature ionic liquids that contain metal halides. (A. P. Abbott, J. C. Barron, K. S. Ryder, D. Wilson, Chem.-Eur. J. 13, 6495 (2007)). Lowering melting points through this way resulted from eutectic effect between metal halide and quaternary ammonium salts. Despite the melting temperature lowering effect, the polarity controls are quite limited in this case because of the presence of metal and halide ions.

Tuning the hydrophobic/hydrophilic balance is another important issue in the aspect of reaction engineering. There are two conventional ways to adjust the hydrophobicity in common ionic liquids. The hydrophobicity of ionic liquid can be raised by increasing alkyl chins in a cation site of ionic liquid. Alternatively, anion substitution can give further adjustment of the hydrophobicity. For example, ionic liquids having an anion, such as $BF_4^-$, $PF_6^-$, or $(CF_3SO_2)_2N^-$, frequently exhibit strong hydrophobicity, which are not readily miscible with water. However, these approaches often cause increases of melting points and viscosity of the ionic liquids as well.

In recent years, ionic liquids have been paid much attention for substitutes of common organic solvent. To satisfy the desirable solvent, they much have a wide range of solubility as well as stability in diverse environments. Most ionic liquids have selective miscibility in either polar or non-polar compounds at room temperature. Ionic liquids with versatile solubility in both polar and non-polar solvent are rarely reported up to now.

The use of ionic liquid containing alkyl sulfate anion as phase transfer catalysts is discussed in U.S. Pat. No 7,252,791. In particular the miscibility with non-polar solvent normally depends on the alkyl group, which is located at either organic cation or sulfate anion. In industrial aspects, those ionic liquids have less economically viable due to the high cost of alkyl sulfate anions.

Taking into account above listed solvent properties, it would be desirable to have ionic liquids with versatile miscibility in a wide range of solvent for chemical reaction, electrochemical applications, and heat and/or charge transfer media. Furthermore, it would be more advantageous to produce the ionic liquids using relatively low cost materials compared to those of the prior art.

SUMMARY OF THE INVENTION

The present invention provides an ionic liquid which is partially or completely miscible with various polar and/or non-polar solvents, and a method of preparing the same.

The present invention also provides an ionic liquid which can be used as a phase transfer catalyst at room temperature, and a method of preparing the same.

The present invention also provides an ionic liquid which can reduce manufacturing costs, and a method of preparing the same.

According to an aspect of the present invention, there is provided an ionic liquid including one or more of the compounds represented by Formula 1 below:

$$(Cat^+)(R'COO^-) \quad \text{(Formula 1)}$$

wherein $Cat^+$ is a cation selected from quaternary ammonium, quaternary phosphonium, sulfonium, imidazolium, pyridinium, pyrazolium, piperidinium, pyrrolium, pyrrolidinium, triazolium, and a mixture of two or more thereof, and R' is a hydrocarbon comprising at least one unsaturated bond, and having 4 to 30 carbon atoms.

The $Cat^+$ may be a cation represented by Formula 2:

$$(R_1R_2R_3R_4Z^+) \quad \text{(Formula 2)}$$

wherein Z is one of nitrogen and phosphorous, and $R_1$, $R_2$, $R_3$, and $R_4$ are each independently one selected from the group consisting of a linear or branched alkyl group, alkylene group, allyl group, benzyl group, phenyl group, and cycloalkyl group.

The $R'COO^-$ may be an anion selected from the group consisting of crotonate group, undecylenate group, myristoleate group, palmitoleate group, oleate group, linoleate group, linolenate group, eicosapentaenoate group, erucate group, arachidonate group, docosahexaenoate group and mixtures thereof.

The ionic liquid may have a melting point of 30° C. or less.

The ionic liquid may be used as a solvent, a solvent additive, a phase transfer catalyst, an electrolyte solution, a heat carrier or a charge carrier, and/or a heat carrier additive or a charge carrier additive.

The ionic liquid may be miscible with a solvent comprising water, alcohols, acids, olefins, paraffins, aromatics, aliphatics, amines, ethers, esters, ketones, aldehydes, amides, nitriles, nitroalkanes, or mixtures thereof.

The ionic liquid may be at least one selected from the group consisting of dimethylbutylhexyl ammonium undecylenate, allyltributyl ammonium undecylenate, triethyloctyl ammonium undecylenate, tripropylbutyl ammonium undecylenate, tripropylhexyl ammonium undecylenate, tripropyloctyl ammonium undecylenate, tributylpropyl ammonium undecylenate, tributylhexyl ammonium undecylenate, tributyloctyl ammonium undecylenate, and hexyltributyl ammonium oleate.

DETAILED DESCRIPTION OF THE INVENTION

Hereinafter, an ionic liquid and a method of preparing the same according to the present invention will be described more fully.

An ionic liquid according to an embodiment of the present invention includes at least one of the compounds represented by Formula 1 below.

(Cat$^+$)(R'COO$^-$)      (Formula 1)

wherein Cat$^+$ may be a cation selected from quaternary ammonium, quaternary phosphonium, sulfonium, imidazolium, pyridinium, pyrazolium, piperidinium, pyrrolium, pyrrolidinium, triazolium, and a mixture of two or more thereof.

Specifically, the Cat$^+$ may be a cation represented by Formula 2:

(R$_1$R$_2$R$_3$R$_4$Z$^+$)      (Formula 2)

wherein Z is one of nitrogen and phosphorous, and R$_1$, R$_2$, R$_3$, and R$_4$ are each independently one selected from the group consisting of a linear or branched alkyl group (preferably C$_1$-C$_8$ alkyl group), alkylene group, allyl group, benzyl group, phenyl group, and cycloalkyl group (preferably C$_3$-C$_8$ cycloalkyl group).

More specifically, the Cat$^+$ may be a heterocyclic quaternary cation selected from the group consisting of imidazolium, pyridinium, piperidinium, pyrrolium, pyrrolidinium, triazolium, and mixtures thereof.

The cation may have a symmetrical or an asymmetrical structure, and particularly in the case of having an asymmetrical structure, the cation may include nitrogen or phosphorous as a core atom, and have a plurality of substituent groups (R$_1$, R$_2$, R$_3$ and R$_4$) where at least one of the substituent groups is different from the other substituent groups.

R' may be a hydrocarbon including at least one unsaturated bond, and having 4 to 30 carbon atoms.

Specifically, the R'COO$^-$ may be an anion selected from the group consisting of crotonate group, undecylenate group, myristoleate group, palmitoleate group, oleate group, linoleate group, linolenate group, eicosapentaenoate group, erucate group, arachidonate group, docosahexaenoate group and mixtures thereof. An undecylenate group or an oleate group is preferable.

In the case where the R'COO$^-$ is an undecylenate group, the ionic liquid may be represented by Formula 3 below:

(Formula 3)

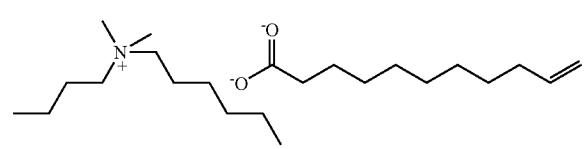

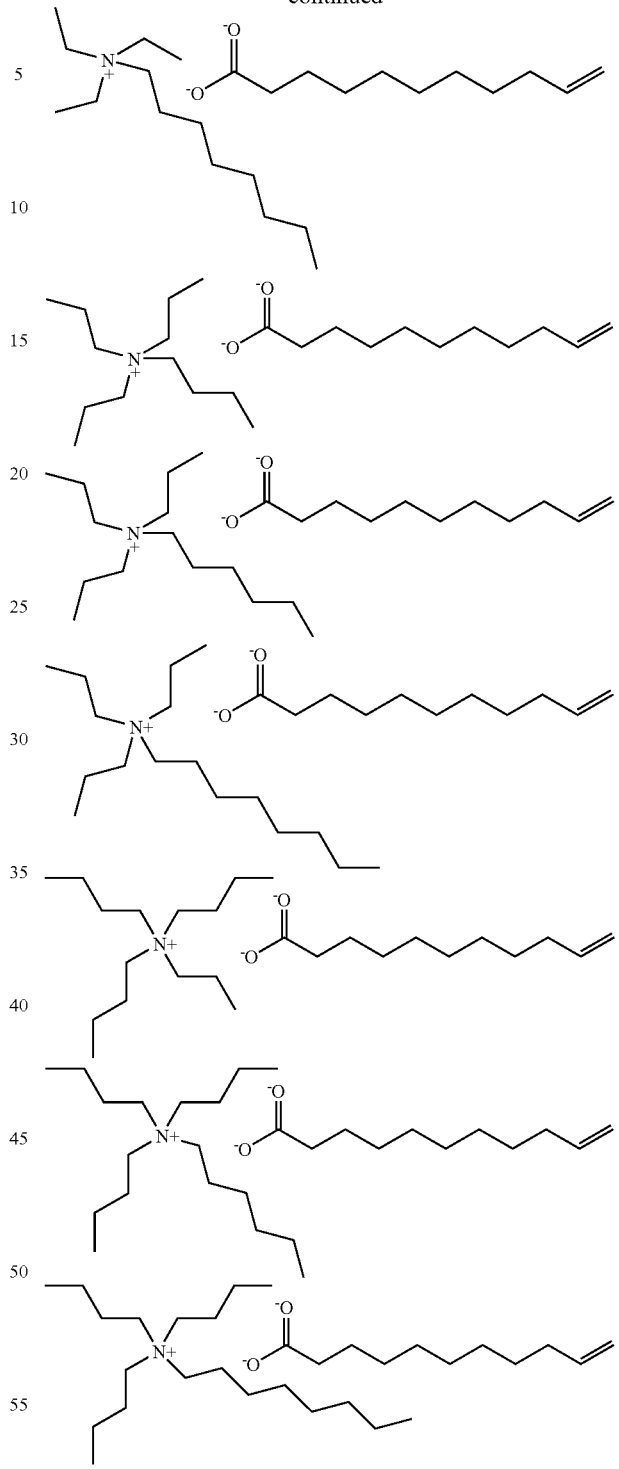

The ionic liquid according to the current embodiment of the present invention is prepared using a process including: synthesizing a cation (Cat$^+$) containing compound; producing a hydroxyl compound by anion-exchanging the cation-containing compound; and quantitizing the hydroxyl compounds and/or neutralizing the hydroxyl compound with a carboxylic acid-containing unsaturated acid. The carboxylic acid-containing unsaturated acid used for forming the anion of the ionic liquid is relatively inexpensive, and therefore the cost of manufacturing the ionic liquid can be greatly reduced.

During the anion exchanging process, methanol may be preferably used as a solvent in order to easily and quickly separate the reaction product. Generally, in such an anion exchange process, the use ratio of ionic liquid: ion exchange resin may preferably be 1:2 to 1:10 based on ionic equivalent weight, and it is desirable to use a large amount of the ionic exchange resin.

The ionic liquid according to the current embodiment of the present invention may be composed of at least one cation and one anion, or may be composed of one cation and at least one anion. Particularly in the case of an ionic liquid composed of one anion and at least one cation, the ionic liquid has many advantages when used as a solvent, a solvent additive, a phase transfer catalyst, an electrolyte, a heat carrier, or a charge carrier. In particular, the reason the ionic liquid can be used as a phase transfer catalyst is because the ionic liquid is partially or completely miscible with two or more solvents which will be described later.

The ionic liquid prepared as described above may have a melting point of 30° C. or less. The ionic liquid may be used as a solvent, a solvent additive, a phase transfer catalyst, an electrolyte solution, a heat carrier or a charge carrier, or a heat carrier additive or a charge carrier additive.

The ionic liquid may be miscible with a solvent such as water, alcohols, acids, olefins, paraffins, aromatics, aliphatics, amines, ethers, esters, ketones, aldehydes, amides, nitrites, nitroalkanes, or mixtures thereof.

Specifically, the ionic liquid may include at least one selected from the group consisting of dimethylbutylhexyl ammonium undecylenate, allyltributyl ammonium undecylenate, triethyloctyl ammonium undecylenate, tripropylbutyl ammonium undecylenate, tripropylhexyl ammonium undecylenate, tripropyloctyl ammonium undecylenate, tributylpropyl ammonium undecylenate, tributylhexyl ammonium undecylenate, tributyloctyl ammonium undecylenate, and hexyltributyl ammonium oleate.

The present invention will now be described in more detail with reference to the following examples. However, these examples are for illustrative purposes only and are not intended to limit the scope of the invention.

EXAMPLES

<Preparation of Ionic Liquid>

Example 1

Preparation of Dimethyl Butyl Hexyl Ammonium Undecylenate

1) Step 1: Synthesis of Dimethylbutylhexyl Ammonium Bromide

Dimethylbutylamine (0.14 mol) was dissolved in acetonitrile (80 ml), and was stirred vigorously at room temperature. Hexyl bromide (0.14 mol) was slowly added to the mixture and was refluxed for 24 hours. Then, the reaction mixture was cooled to room temperature, and the solvent (acetonitrile) was removed using a rotary evaporator. The remaining non-reacted material was extracted three times using diethyl ether (150 ml) for purification. The obtained product was dried under vacuum for 24 hours. As a result, a yellow liquid (38 g) was obtained. A nuclear magnetic resonance (NMR) analysis result of the liquid was as follows.

NMR analysis result: 1H NMR (CDCl$_3$, 400 MHz) 3.42(m, 4H), 3.25(s, 6H), 1.59(m, 4H), 1.28(m, 8H), 0.88(t, 3H), 0.77(t, 3H)

2) Step 2: Preparation of Dimethyl Butyl Hexyl Ammonium Hydroxide

An anion exchange resin (LANXESS, M800-KR, 100 ml) filled in a column (glass of 250 ml-capacity) was washed with distilled water until the pH became neutral. Then, the anion exchange resin was washed additionally with methanol. Next, the dimethyl butyl hexyl ammonium bromide (0.038 mol) synthesized in Step 1 was dissolved in a small amount of methanol (50 ml) and was slowly passed through the anion exchange resin column. Then, excess methanol was passed through the anion exchange resin column until the pH of the anion exchange resin became neutral. After passing through the anion exchange resin column, the dimethyl butyl hexyl ammonium bromide was converted into dimethyl butyl hexyl ammonium hydroxide. In order to verify the product, 3 ml of the crude product was taken and methanol was evaporated and completely removed therefrom using a rotary evaporator. Next, the product was verified to be dimethyl butyl hexyl ammonium hydroxide by using NMR, after the vacuum drying.

3) Step 3: Quantification of Dimethyl Butyl Hexyl Ammonium Hydroxide

In order to determine a stoichiometric amount of acid required to neutralize the dimethyl butyl hexyl ammonium hydroxide, the dimethyl butyl hexyl ammonium hydroxide containing methanol solution was titrated with 1N HCl. As a result of the titration, the concentration of the dimethyl butyl hexyl ammonium hydroxide in the methanol solution was determined to be 0.1 M.

4) Step 4: Preparation of Dimethyl Butyl Hexyl Ammonium Undecylenate

The dimethyl butyl hexyl ammonium hydroxide and undecylenic acid were mixed in a molar ratio of 1:1, and stirred for 1 hour. Here, the amount of undecylenic acid was calculated based on the titration result obtained in Step 3. Methanol was removed from the reaction mixture using a rotary evaporator. Next, the reaction mixture was dried under vacuum for 12 hours for an additional purification. As a result, a clear brown liquid was obtained. An NMR analysis result of the liquid was as below:

NMR analysis result: 1H NMR (CDCl$_3$, 400 MHz) 5.70(m, 1H), 4.90(dd, 2H), 3.32(m, 4H), 3.25(s, 6H), 2.06(t, 2H), 1.91(m, 2H), 1.57(m, 4H), 1.27(m, 20H), 0.90(t,3H), 0.80(t, 3H)

Examples 2 and 3

An ionic liquid was prepared using the same method as in Example 1, except that an amine ($R_1R_2R_3N$) and an alkyl bromide ($R_4$—Br) according to Table 1 below were used in step 1, and the product was washed with diethyl ether, and a filtration was additionally performed in order to separate out the product. That is, because a white solid-phase product was obtained before purification, the product was washed with diethyl ether and an additional filtration was performed in order to recover the product.

Examples 4 to 8

An ionic liquid was prepared using the same method as in Example 1, except that an amine ($R_1R_2R_3N$) and an alkyl bromide ($R_4$—Br) according to Table 1 below were used in step 1.

Example 9

An ionic liquid was prepared using the same method as in Example 1, except that an amine ($R_1R_2R_3N$) and an alkyl bromide ($R_4$—Br) according to Table 1 below were used in step 1, and oleic acid was used instead of undecylenic acid in step 4.

TABLE 1

| Examples | $R_1$ | $R_2$ | $R_3$ | $R_4$ | Anion |
|---|---|---|---|---|---|
| 1 | $CH_3$ | $CH_3$ | $C_4H_9$ | $C_6H_{13}$ | $CH_2$=$CH(CH_2)_8COO$— (Undecylenate) |
| 2 | $C_2H_5$ | $C_2H_5$ | $C_2H_5$ | $C_8H_{17}$ | $CH_2$=$CH(CH_2)_8COO$— (Undecylenate) |
| 3 | $C_3H_7$ | $C_3H_7$ | $C_3H_7$ | $C_4H_9$ | $CH_2$=$CH(CH_2)_8COO$— (Undecylenate) |
| 4 | $C_3H_7$ | $C_3H_7$ | $C_3H_7$ | $C_6H_{13}$ | $CH_2$=$CH(CH_2)_8COO$— (Undecylenate) |
| 5 | $C_3H_7$ | $C_3H_7$ | $C_3H_7$ | $C_8H_{17}$ | $CH_2$=$CH(CH_2)_8COO$— (Undecylenate) |
| 6 | $C_4H_9$ | $C_4H_9$ | $C_4H_9$ | $C_3H_7$ | $CH_2$=$CH(CH_2)_8COO$— (Undecylenate) |
| 7 | $C_4H_9$ | $C_4H_9$ | $C_4H_9$ | $C_6H_{13}$ | $CH_2$=$CH(CH_2)_8COO$— (Undecylenate) |
| 8 | $C_4H_9$ | $C_4H_9$ | $C_4H_9$ | $C_8H_{17}$ | $CH_2$=$CH(CH_2)_8COO$— (Undecylenate) |
| 9 | $C_4H_9$ | $C_4H_9$ | $C_4H_9$ | $C_6H_{13}$ | $CH_3(CH_2)_7CH$=$CH(CH_2)_7COO$— (Oleate) |

NMR results of the products obtained from steps 1 and 4 of Examples 2 to 9 are as follows:

Step 1 of Example 2:
1H NMR ($CDCl_3$, 400 MHz) 3.33(m, 6H), 3.11(m, 2H), 1.70(m, 2H), 1.15(m, 19H), 0.71(t, 3H)

Step 4 of Example 2:
1H NMR ($CDCl_3$, 400 MHz) 5.56(m, 1H), 4.69(dd, 2H), 3.21(m, 8H), 2.96(m, 2H), 1.94(m, 2H), 1.78(m, 2H), 1.35(m, 4H), 1.09(m, 29H), 0.64(t, 3H)

Step 1 of Example 3:
1H NMR ($CDCl_3$, 400 MHz) 3.36(m, 8H), 1.69(m, 8H), 1.45(q, 2H), 1.00(m, 12H)

Step 4 of Example 3:
1H NMR ($CDCl_3$, 400 MHz) 5.75(m, 1H), 4.88(dd, 2H), 3.21 (m, 8H), 2.13(t, 2H), 1.97(q, 2H), 1.62(m, 10H), 1.33(m, 12H), 0.97(m, 12H)

Step 1 of Example 4:
1H NMR ($CDCl_3$, 400 MHz) 3.08(m, 8H), 1.50(m, 8H), 1.12(m, 6H), 0.83(t, 3H), 0.67(t, 3H)

Step 4 of Example 4:
1H NMR($CDCl_3$, 400 MHz) 5.74(m, 1H), 4.87(dd, 2H), 3.25(m, 8H), 2.12(t, 2H), 1.96(m, 2H), 1.62(m, 8H), 1.25(m, 18H), 0.98(t, 9H), 0.84(t, 3H)

Step 1 of Example 5:
1H NMR ($CDCl_3$, 400 MHz) 3.29(m, 8H), 1.67(m, 6H), 1.22 (m, 10H), 0.97(t, 9H), 0.78(t, 3H)

Step 4 of Example 5:
1H NMR ($CDCl_3$, 400 MHz) 5.69(m, 1H), 4.83(dd, 2H), 3.19(m, 8H), 2.13(t, 2H), 1.91(m, 2H), 1.64(m, 10H), 1.18(m, 20H), 0.92(t, 9H), 0.77(t, 3H)

Step 1 of Example 6:
1H NMR ($CDCl_3$, 400 MHz) 3.10(m, 8H), 1.50(m, 8H), 1.20(m, 6H), 0.73(m, 12H)

Step 4 of Example 6:
1H NMR ($CDCl_3$, 400 MHz) 5.74(m, 1H), 4.90(dd, 2H), 3.27(m, 8H), 2.11(t, 2H), 1.96(q, 2H), 1.61(m, 8H), 1.30(m, 18H), 0.94(m, 12H)

Step 1 of Example 7:
1H NMR ($CDCl_3$, 400 MHz) 3.27(m, 8H), 1.57(m, 8H), 1.26(m, 12H), 0.90(t, 9H), 0.78(t, 3H)

Step 4 of Example 7:
1H NMR ($CDCl_3$, 400 MHz) 5.74(m, 1H), 4.87(dd, 2H), 3.31(m, 8H), 2.19(m, 2H), 1.98(q, 2H), 1.58(m, 8H), 1.37(m, 24H), 0.90(m, 9H), 0.88(m, 3H)

Step 1 of Example 8:
1H NMR ($CDCl_3$, 400 MHz) 3.33(m, 8H), 1.64(m, 8H), 1.18(m, 18H), 0.97(t, 9H), 0.84(t, 3H)

Step 4 of Example 8:
1H NMR ($CDCl_3$, 400 MHz) 5.74(m, 1H), 4.87(dd, 2H), 3.28(m, 8H), 2.11(t, 2H), 1.96(m, 2H), 1.58(m, 10H), 1.33(m, 28H), 0.94(t, 9H), 0.82(t, 3H)

Step 1 of Example 9:
1H NMR ($CDCl_3$, 400 MHz) 3.27(m, 8H), 1.57(m, 8H), 1.34(m, 12H), 0.90(t, 3H), 0.78(t, 3H)

Step 4 of Example 9:
1H NMR ($CDCl_3$, 400 MHz) 5.29(m, 2H), 3.26(m, 8H), 2.20(t, 2H), 1.96(m, 4H), 1.59(m, 10H), 1.38(m, 40H), 0.95(t, 3H), 0.83(m, 9H)

<Evaluation of Solubility of the Ionic Liquids>

Solubility of the ionic liquids in water or non-polar organic solvents were evaluated, by mixing the ionic liquids prepared in Examples 1 to 9 with water or various non-polar organic solvents in a molar ratio of 1:1. The amount of ionic liquid and water or non-polar organic solvent used was 0.003 mol each, and for a good mixing, the mixtures were let sit in a mixed state at 50° C. for 1 day, and then cooled to room temperature to observe the solubility of each case. The solubility results of the ionic liquids prepared in Examples 1 to 9 in water or organic solvents are shown in Table 2. Meanwhile, it is well known to those of ordinary skill in the art that such ionic liquids mix completely with most polar solvents. Thus, the solubility of the ionic liquids in polar organic solvents such as methanol, ethanol, acetone, dichloromethane, or ethylacetate was not evaluated separately.

TABLE 2

| Example | Water | Hexane | Methyl cyclo hexane | 2-methyl-1-butyne | pentane | heptane | toluene | cyclohexane | 2-methyl butane | 1-hexane |
|---|---|---|---|---|---|---|---|---|---|---|
| 1 | Y | Y | Y | Y | Y | Y | Y | Y | Y | Y |
| 2 | Y | P | Y | Y | Y | P | Y | Y | Y | Y |
| 3 | Y | P | P | N | P | N | Y | Y | P | P |
| 4 | Y | Y | Y | Y | Y | Y | Y | Y | Y | Y |
| 5 | Y | Y | Y | Y | Y | Y | Y | Y | Y | Y |
| 6 | Y | P | P | Y | P | P | Y | Y | P | Y |
| 7 | Y | Y | Y | Y | Y | Y | Y | Y | Y | Y |

TABLE 2-continued

| Example | Water | Hexane | Methyl cyclo hexane | 2-methyl-1-butyne | pentane | heptane | toluene | cyclohexane | 2-methyl butane | 1-hexane |
|---|---|---|---|---|---|---|---|---|---|---|
| 8 | Y | Y | Y | Y | Y | Y | Y | Y | Y | Y |
| 9 | Y | Y | Y | Y | Y | Y | Y | Y | Y | Y |

Y: Miscible,
N: Not miscible,
P: Partially miscible

Referring to Table 2, it can be seen that the ionic liquids prepared in Examples 1 to 9 according to the present invention mixed well with water and most of the non-polar organic solutions. That is, an ionic liquid which is partially or completely miscible with most polar and non-polar solvents can be prepared according to the present invention.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ionic liquid comprising at least one of the compounds represented by Formula 1 below:

(Cat$^+$)(R'COO$^-$)  (Formula 1)

wherein Cat$^+$ is a cation selected from the group consisting of quaternary ammonium, quaternary phosphonium, sulfonium, imidazolium, pyridinium, pyrazolium, piperidinium, pyrrolium, pyrrolidinium, triazolium, and a mixture of two or more thereof, and R' is a hydrocarbon comprising at least one unsaturated bond, and having 4 to 30 carbon atoms such that R'COO$^-$ is an anion selected from the group consisting of crotonate group, undecylenate group, myristoleate group, palmitoleate group, oleate group, eicosapentaenoate group, erucate group, arachidonate group, docosahexaenoate group, and mixtures thereof, wherein when the R'COO$^-$ is oleate and Cat$^+$ is quaternary ammonium, Cat$^+$ is hexyl tributyl ammonium.

2. The ionic liquid of claim 1, wherein the Cat$^+$ is a cation represented by Formula 2:

(R$_1$R$_2$R$_3$R$_4$Z$^+$)  (Formula 2)

wherein Z is one of nitrogen and phosphorous, and R$_1$, R$_2$, R$_3$, and R$_4$ are each independently one selected from the group consisting of a linear or branched alkyl group, alkylene group, allyl group, benzyl group, phenyl group, and cycloalkyl group.

3. The ionic liquid of claim 1, wherein the ionic liquid has a melting point of 30° C. or less.

4. The ionic liquid of claim 1, wherein the ionic liquid is used as one selected from the group consisting of a solvent, a solvent additive, a phase transfer catalyst, an electrolyte solution, a heat or charge carrier, and a heat carrier or charge carrier additive.

5. The ionic liquid of claim 1, wherein the ionic liquid is miscible with a solvent comprising one selected from the group consisting of water, alcohols, acids, olefins, paraffins, aromatics, aliphatics, amines, ethers, esters, ketones, aldehydes, amides, nitriles, nitroalkanes, and mixtures thereof.

6. The ionic liquid of claim 1, wherein the ionic liquid comprises at least one selected from the group consisting of dimethylbutylhexyl ammonium undecylenate, allyltributyl ammonium undecylenate, triethyloctyl ammonium undecylenate, tripropylbutyl ammonium undecylenate, tripropylhexyl ammonium undecylenate, tripropyloctyl ammonium undecylenate, tributylpropyl ammonium undecylenate, tributylhexyl ammonium undecylenate, tributyloctyl ammonium undecylenate, and hexyltributyl ammonium oleate.

7. A method of preparing an ionic liquid according to claim 1, the method comprising:
    preparing a cation (Cat$^+$) containing compound;
    producing a hydroxyl compound by anion exchanging the cation-containing compound; and
    neutralizing the hydroxyl compound with a carboxylic acid-containing unsaturated acid of the formula R'COOH,
    wherein R' is a hydrocarbon comprising at least one unsaturated bond, such that R'COO$^-$ is an anion selected from the group consisting of crotonate group, undecylenate group, myristoleate group, palmitoleate group, oleate group, eicosapentaenoate group, erucate group, arachidonate group, docosahexaenoate group and mixtures thereof,
    wherein when R'COO$^-$ is oleate and Cat$^+$ is quaternary ammonium, Cat$^+$ is hexyl tributyl ammonium.

* * * * *